(12) United States Patent
Malin et al.

(10) Patent No.: US 7,886,605 B2
(45) Date of Patent: Feb. 15, 2011

(54) CONFORMABLE ULTRASONIC ARRAY APPARATUS

(75) Inventors: Brian Keith Malin, St. Louis, MO (US); Terry Lynn Versheldon, St Charles, MO (US); Eugene Arthur Myers, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 498 days.

(21) Appl. No.: 12/050,697

(22) Filed: Mar. 18, 2008

(65) Prior Publication Data

US 2009/0235751 A1 Sep. 24, 2009

(51) Int. Cl.
G01N 29/00 (2006.01)
G01N 29/04 (2006.01)

(52) U.S. Cl. .......................................... 73/644; 73/649
(58) Field of Classification Search .................... 73/644, 73/636, 649, 583, 661, 596, 614, 624–627
See application file for complete search history.

(56) References Cited

U.S. PATENT DOCUMENTS

| | | | | | |
|---|---|---|---|---|---|
| 3,958,451 | A | * | 5/1976 | Richardson | 73/644 |
| 3,960,005 | A | * | 6/1976 | Vezina | 73/614 |
| 4,012,946 | A | * | 3/1977 | Patsey | 73/627 |
| 4,242,744 | A | * | 12/1980 | Rottmar | 367/173 |
| 4,421,118 | A | * | 12/1983 | Dow et al. | 600/446 |
| 7,637,163 | B2 | * | 12/2009 | Fetzer et al. | 73/644 |
| 2007/0175282 | A1 | * | 8/2007 | Fetzer et al. | 73/649 |
| 2007/0239018 | A1 | | 10/2007 | Fetzer et al. | |
| 2008/0202245 | A1 | | 8/2008 | Young | |

* cited by examiner

Primary Examiner—Helen C. Kwok
(74) Attorney, Agent, or Firm—Yee & Associates, P.C.; Dennis R. Plank

(57) ABSTRACT

A method and apparatus for ultrasonic inspection. The ultrasonic inspection apparatus comprises ultrasonic transducers, a body, a set of engagement members and a set of ports. The ultrasonic transducers are at a position generally adjacent to a surface of an object. The body has a contact surface capable of contacting the surface and is capable of holding the set of ultrasonic transducers. The engagement members are connected to the body for engagement with the surface. The engagement members are flexibly bendable and are conformed to contours across the surface to form a coupling region within the body. The set of ports deliver a coupling material to the coupling region. The engagement members, when in contact with the surface of the object, cause a seal to retain an amount of the coupling material within the coupling region sufficient to couple the ultrasonic transducers to the surface.

18 Claims, 8 Drawing Sheets

CONFORMABLE ULTRASONIC ARRAY APPARATUS

BACKGROUND INFORMATION

1. Field

The present disclosure relates generally to ultrasonic inspection and in particular to a method and apparatus for identifying undesirable conditions in an object using ultrasonic inspection. Still more particularly, the present disclosure relates to a method and apparatus for positioning ultrasonic transducers generally adjacent to the surface of an object.

2. Background

Aircraft are being designed and manufactured with greater percentages of composite materials. Some aircraft may have more than fifty percent of their primary structure made from composite materials. Composite materials are being used in aircraft to decrease the weight of the aircraft. This decreased weight improves payload capacities and fuel efficiencies. Further, composite materials also may provide improved corrosion and fatigue resistance for various components in an aircraft.

Composite materials are tough, light-weight materials created by combining two or more dissimilar components to create a component with stronger properties than the original materials. Composite materials are typically non-metal materials. For example, a composite may include fibers and resins. The fibers and resins may be combined by curing or heating these components to form a cured product for the composite material.

In particular, key components, such as wings and fuselage skins, are now being constructed exclusively with composite materials, such as a composite laminate. With more and more critical structures being made of composite laminates, methods and techniques to assure that these components meet quality standards are needed more than ever before.

Porosity is an example of known undesirable condition that may occur during processing to create composite components. Porosity occurs when voids are present in a material caused by evolved gases. Currently, much time, effort, and money is spent on ultrasonic measurement systems that are designed to detect and quantify the porosity in composite components, such as those made using carbon laminates. Other examples of undesirable conditions include, for example, the presence of foreign materials or debris within the component and delamination.

Ultrasonic testing involves sending ultrasonic pulse waves into an object to detect undesirable conditions or to characterize materials. In ultrasonic testing, one or more ultrasound transducers are passed over an object that is being inspected. The transducers are typically separated from the test object by a coupling material. This coupling material may be, for example, a liquid such as oil or water. The same ultrasound transducer may send and receive ultrasound signals. In other advantageous embodiments, one ultrasound transducer may be used to transmit the ultrasound through the surface while a separate receiver detects the ultrasound that has reached the other surface after travelling through a medium. The coupling material is used to prevent signal loss. In this manner, undesirable conditions may be detected.

Typically, the ultrasound transducer or transducers are placed into a housing that positions the ultrasound transducer over the object. The design of the housing may be such to allow a maximum area of inspection. Maintaining the coupling between the transducer and the surface of the object may be challenging in some situations. For example, if the object being tested is too large to immerse within the coupling material, the housing may supply the coupling material in the manner to maintain the coupling material between the transducer and the surface of the object.

Retaining or maintaining sufficient coupling material may be performed through the design of the housing. Many designs are suitable for use on flat surfaces. However, when the same housing is used on a curved surface, is often difficult to maintain sufficient coupling thread to perform an inspection. This type of situation may occur with the fuselage of an aircraft. If the housing containing the transducer is moved longitudely, the surface maintains a constant curve. If the housing is turned to move around the longitudinal axis, then the shape of the housing may no longer fit the curvature of the surface. In this case, a different housing may be needed.

One solution currently used for this problem is to employ a bladder. The bladder encapsulates or contains the coupling material and is placed between the housing and the surface of the object. One drawback of the bladder is increased friction on the surface on the part. This type of friction may cause the housing to move in a manner that causes a loss in the ultrasonic signal.

Further, the use of a bladder requires more area around a transducer to incorporate the bladder into the housing design. The increased area around the transducer also may result in loss inspection area near the edges of the part to be inspected. Further, with a bladder it is important that all of the air is removed from the bladder before the inspection begins. Therefore, it would be advantageous to have an improved method and apparatus for performing ultrasonic inspections of objects.

SUMMARY

The advantageous embodiments provide a method and apparatus for ultrasonic inspection. The ultrasonic inspection apparatus comprises a set of ultrasonic transducers, a body, a set of engagement members and a set of ports. The set of ultrasonic transducers are at a position generally adjacent to a surface of an object. The body has a contact surface capable of contacting the surface of the object, wherein the body is capable of holding the set of ultrasonic transducers. The set of engagement members are connected to the body for engagement with the surface of the object, wherein the set of engagement members are flexibly bendable and are capable of conforming to contours across the surface of the object to form a coupling region within the body. The set of ports is capable of delivering a coupling material to the coupling region and wherein the set of engagement members, when in contact with the surface of the object, cause a seal to retain an amount of the coupling material within the coupling region sufficient to couple the set of ultrasonic transducers to the surface of the object.

In another advantageous embodiment, a housing has a contact surface capable of contacting the surface of the object, wherein the housing is capable of holding a set of ultrasonic transducers. A set of engagement members is coupled to the housing, wherein the set of engagement members is capable of engaging the surface of the object, wherein the set of engagement members is flexibly bendable and is capable of conforming to contours across the surface of the object to form a coupling region in which a coupling material can be retained when the contact surface of the housing is in contact with the surface of the object.

In still another advantageous embodiment, a method is present for inspecting the object. An inspection apparatus is placed on a surface of the object, wherein the inspection apparatus comprises the set of transducers, a body, a set of engagement members, and a set of ports, the body has a contact surface capable of contacting the surface of the object, wherein the body is capable of holding the set of ultrasonic transducers. The set of engagement members is coupled to the body for engagement with the surface of the object, wherein the set of engagement members is flexibly bendable and is capable of conforming to contours across the surface of the object to form a coupling region within the body. The set of ports is capable of delivering a coupling material to the coupling region and wherein the set of engagement members, when the set of engagement members are in contact with the surface of the object, causes a seal to retain an amount of the coupling material within the coupling region sufficient to couple the set of ultrasonic transducers to the surface of the object to send signals into object and receive ultrasonic signals from the object. The inspection apparatus is coupled to the object to form a coupled inspection apparatus. Ultrasonic signals are sent from the set of transducers in the coupled inspection apparatus. Responses are received to the ultrasonic signals.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
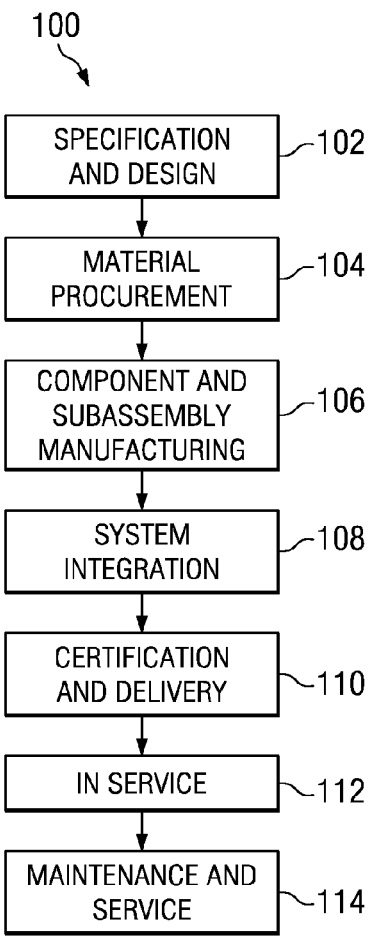
FIG. 1 is a diagram illustrating an aircraft manufacturing and service method in which an advantageous embodiment may be implemented.
Figure 2:
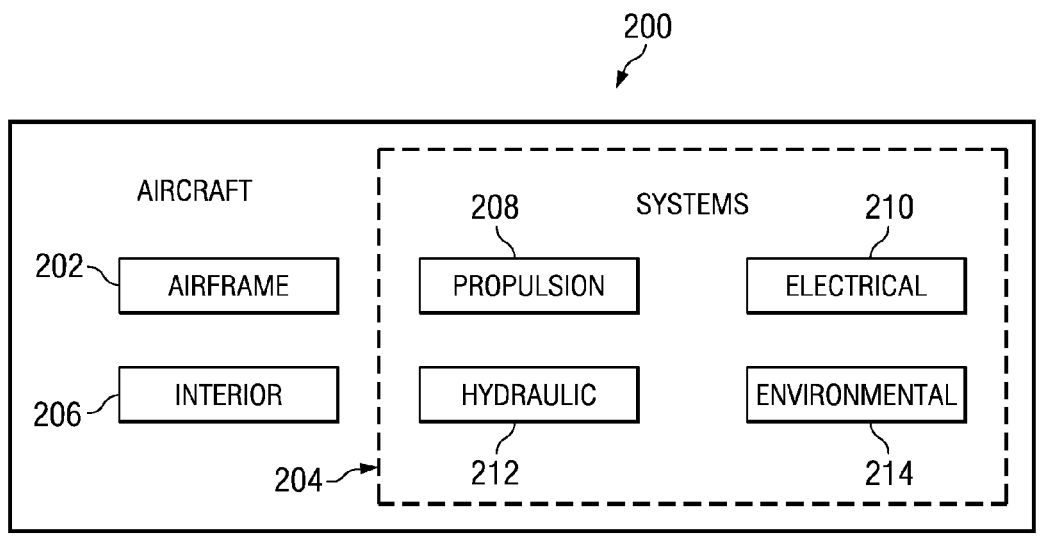
FIG. 2 is a diagram of an aircraft in which an advantageous embodiment may be implemented.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104. During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed to inspect a part during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. For example, the different advantageous embodiments may be implemented during component and subassembly manufacturing 106 to test various components, such as composite components for undesirable conditions. Similarly, one or more of apparatus embodiments, method embodiments, or a combination thereof may be utilized while aircraft 200 is in service 112 or during maintenance and service 114 in FIG. 1.

Figure 3:
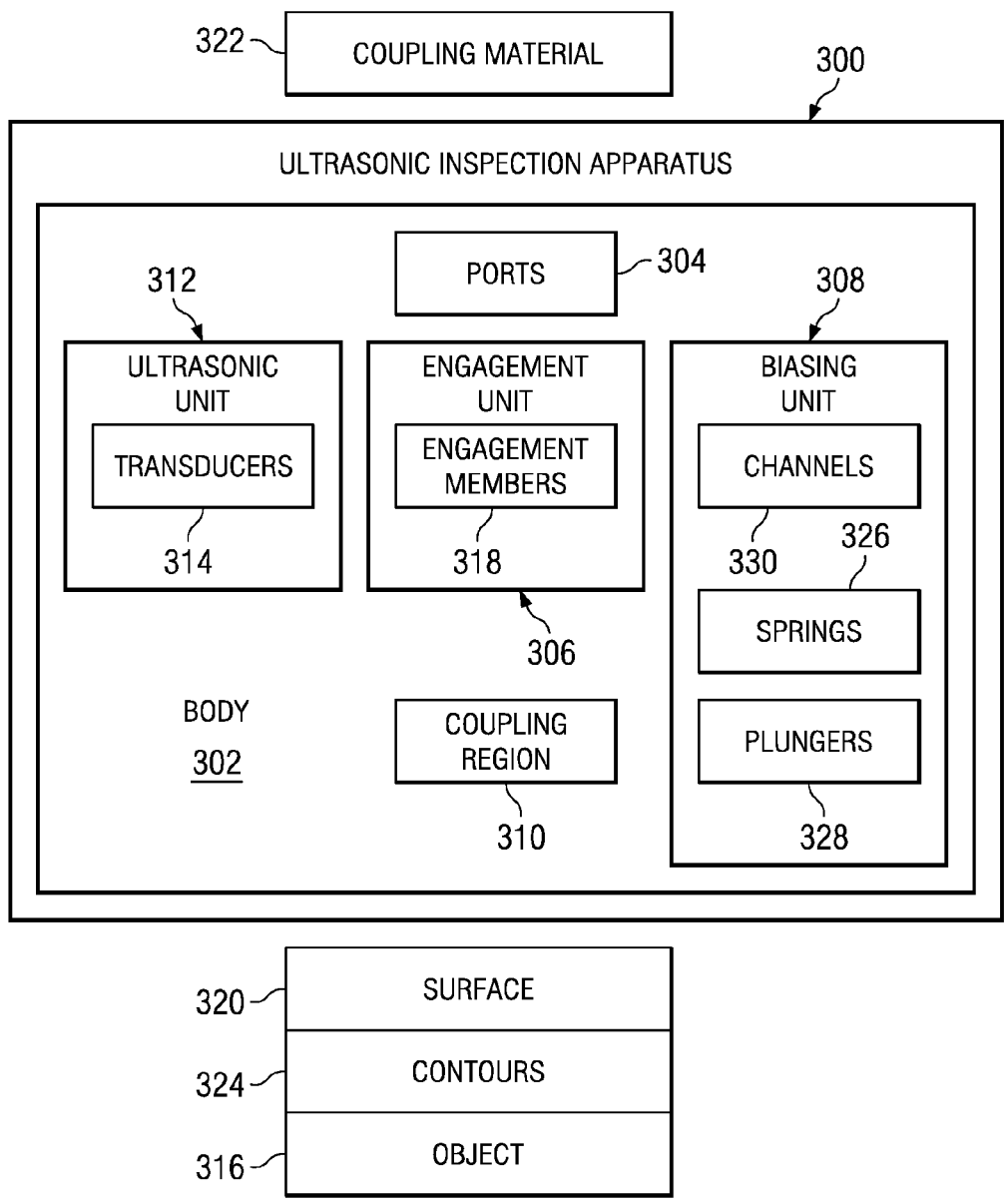
FIG. 3 is a diagram of an ultrasonic inspection apparatus in accordance with an advantageous embodiment.

With reference now to FIG. 3, a diagram of an ultrasonic inspection apparatus is depicted in accordance with an advantageous embodiment. In this example, ultrasonic inspection apparatus 300 is an example of a componentable ultrasonic array shoe. Ultrasonic inspection apparatus 300 includes body 302. In these examples, body 302 is a housing that provides a structural integrity for ultrasonic inspection apparatus 300. This component contains ports 304, engagement unit 306, biasing unit 308, and coupling region 310. Body 302 also may receive ultrasonic unit 312. Some examples of materials for body 302 include, without limitation, polymers such as Teflon® fluoropolymer resins, acetyl, acrylic, polycarbonate, polyethylene, and polyvinyl chloride (PVC). The materials also may include metals such as aluminum, brass, and steel.

Ultrasonic unit 312 in these examples contains transducers 314. These transducers are used to send ultrasonic signals into object 316 when body 300 is placed into contact with object 316. In these examples, transducers 314 are an array of transducers in a housing that may be placed into body 302. In other advantageous embodiments, a single transducer also may be used.

Engagement unit 306 includes engagement members 318. These engagement members are used to cause a seal within coupling region 310 when engagement members 318 are in contact with surface 320 of object 316. This seal is sufficient to retain an amount of coupling material 322 within coupling region 310 to couple transducers 314 to surface 320 of object 316 to allow sending of ultrasonic signals into object 316. In these examples, coupling material 322 may be a liquid, such as, for example, water or an oil.

Of course, other coupling materials may be used in other embodiments. In these examples, engagement members may be made of plastic. Other materials that may be used include polymers such as, for example, without limitation, Teflon® fluoropolymer resins, acetyl, acrylic, polycarbonate, polyethylene, and polyvinyl chloride (PVC). The materials also may include metals, such as aluminum, brass, and steel.

Ultrasonic unit 312 also may receive responses to these ultrasonic signals. In other advantageous embodiments, the signals may be detected by another device. Engagement members 318 are flexibly bendable and capable of conforming to contours 324 in surface 320 of object 316. Engagement members 318 may include different numbers of engagement members depending on the particular implementation. In these illustrative examples, engagement members 318 contain two engagement members.

In other advantageous embodiments, engagement members 318 may contain three engagement members, four engagement members, or some other number of engagement members. These members also may be implemented in other orientations other than those illustrated in these examples. Further, depending on the particular implementation, engagement unit 306 may contain a single engagement member to provide the seal in coupling region in 310. Coupling region 310 is the region in which coupling material 322 is located.

In these examples, engagement members 318 also have a low enough coefficient of friction to allow engagement members 318 to move over object 316. In these examples, the coefficient of friction may be, for example, in a range from about 0 to about 0.5. Other values or ranges may be used depending on the implementation. The different coefficients of friction may be obtained through the use of materials and/or design. For example, the design of the body and body holding mechanism (not shown) may compensate for large range of coefficient of friction.

In some advantageous embodiments, engagement members 318 have a coefficient of friction that allows engagement members 318 to slide on object 316 while creating a seal in coupling region 310 to retain coupling material 322 within coupling region 310. In some cases, when coupling material 322 takes the form of a liquid, losses of coupling material 322 may occur in coupling region 310. The introduction, however, of coupling material 322 is sufficient along with the seal created by engagement members 318 to maintain coupling transducers 314 to surface 320. Further, transducers 314 also are located within coupling region 310 to allow these transducers to couple to surface 320 of object 316 while coupling material 322 is present. Coupling material 322 is introduced into coupling region 310 through ports 304.

Biasing unit 308 is coupled to engagement unit 306 and body 302 in a manner that biasing unit 308 biases or moves engagement unit 306 to contact surface 320. In these examples, biasing unit 306 includes springs 326 and plungers 328. Plungers 328 may provide the connection between springs 326 to engagement members 318 in these examples. Springs 326 may be located within channels 330 within biasing unit 308. When plungers 328 are used, the arrangement is such that springs 326 remain within channels 330.

Of course, other biasing structures or mechanisms can be used in addition to or in place of springs 326. For example, without limitation, leaf springs, rubber members, or other suitable components may be used. When using other types of springs or materials, plungers 328 and/or channels 330 may or may not be used.

In these examples, the connection between springs 326 or plungers 328 to engagement members 318 may not be a fixed connection. Instead, these components may be connected or coupled to engagement members 318 through contact with the surface of engagement members 318. In other words, springs 326 or plungers 328 are biased by springs 326 into contact with engagement members 318. The coupling or connections in engagement members 318 do not require these components to be secured to engagement members 318. In other embodiments, springs 326 may be secured or attached to engage members 318.

Although, in some advantageous embodiments, springs 326 or plungers 328 may be secured to engagement members 318. In the different advantageous embodiments, body 302 functions to maintain the orientation of ultrasonic transducers 314 in ultrasonic unit 312 such that the quality of the received signals is sufficient.

Figure 4:
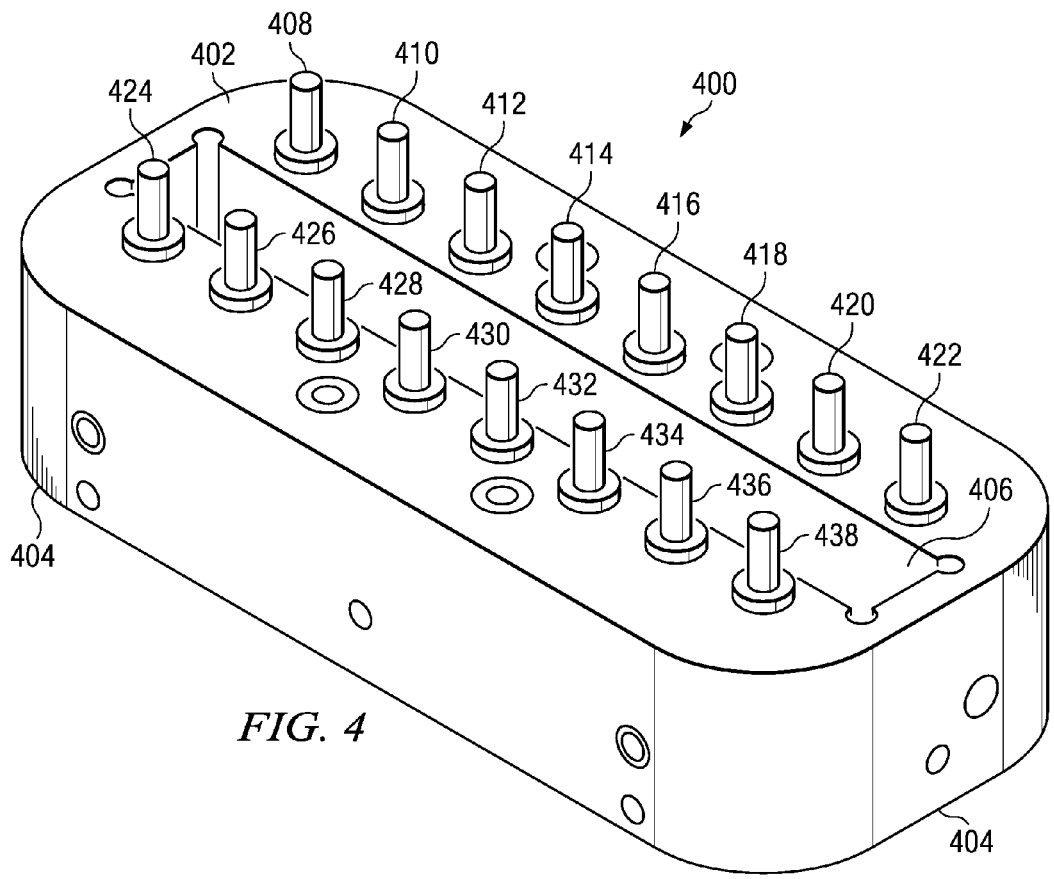
FIG. 4 is a diagram of a perspective view of an ultrasonic inspection apparatus in accordance with an advantageous embodiment.

Turning now to FIG. 4, a diagram of a perspective view of an ultrasonic inspection apparatus is depicted in accordance with an advantageous embodiment. In this example, housing 400 is also referred to as a shoe for the ultrasonic inspection apparatus. Housing 400 has top 402 and bottom 404. Bottom 404 is the side of housing 400 that contacts an object for inspection. Housing 400 also has channel 406. Channel 406 is configured to receive an ultrasonic unit, such as ultrasonic unit 412 in FIG. 4. Housing 400 also includes ports 408, 410, 412, 414, 416, 418, 420, 422, 424, 426, 428, 430, 432, 434, 436, and 438.

Other numbers of ports may be used in other embodiments. For example, a single port or four ports may be used. These ports are designed to receive a coupling material and channel to a coupling region within housing 400. This coupling region is shown in more detail in FIGS. 5 and 6 below.

Figure 5:
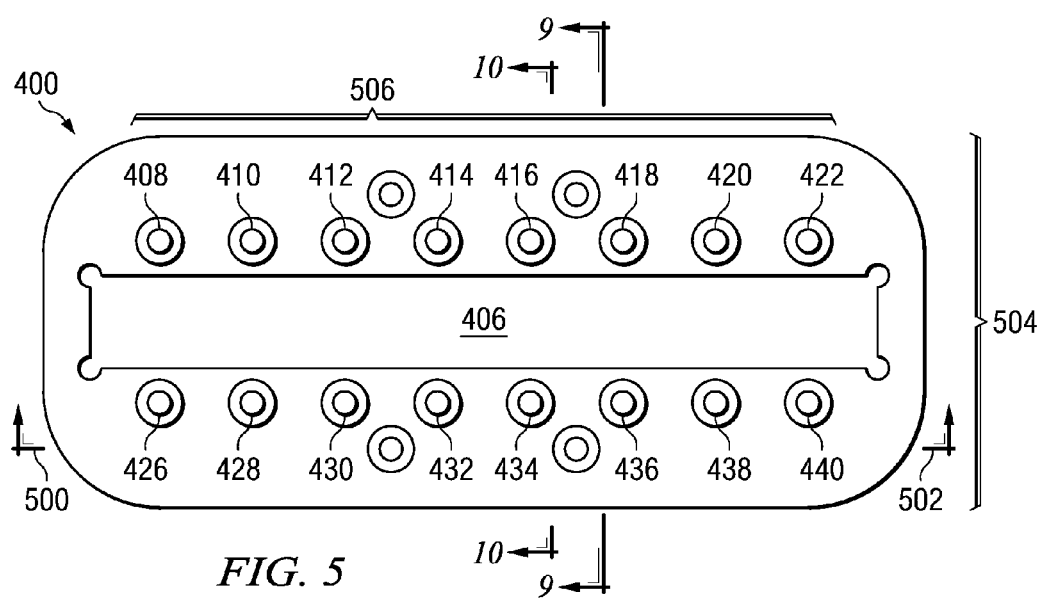
FIG. 5 is a top view of a housing for an ultrasonic inspection apparatus in accordance with an advantageous embodiment.

Turning now to FIG. 5, a top view of a housing for an ultrasonic inspection apparatus is depicted in accordance with an advantageous embodiment. Lines 500-502 identify the orientation of a cross-sectional view in FIG. 6 below. In this illustrative embodiment, the dimensions of housing 400 may vary depending on the particular implementation. In these examples, housing 400 may be, for example, around 1.56 inches in section 504 and around 3.9 inches in section 506. Further, housing 400 may be around one inch tall. Of course, housing 400 may have other dimensions depending on the particular implementation and use.

Figure 6:
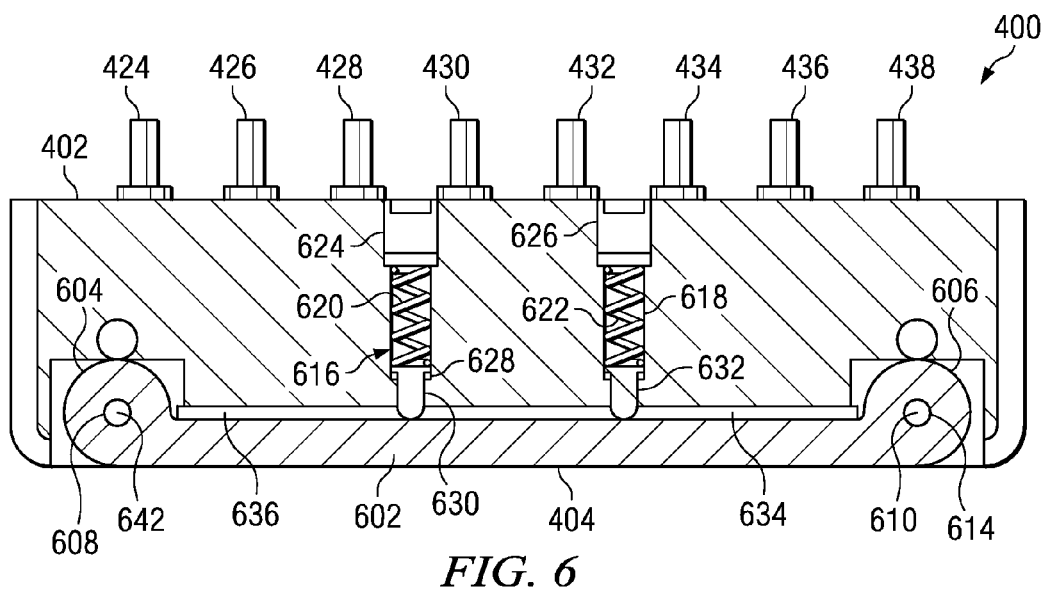
FIG. 6 is a cross-sectional view of a housing in accordance with an advantageous embodiment.

With reference now to FIG. 6, a cross-sectional view of a housing is depicted in accordance with an advantageous embodiment. In this example, housing 400 is shown in cross-sectional view taken along lines 500 and 502 in FIG. 5.

In this example, flex beam 602 is one of two flex beams that are present within housing 400 in this example. Flex beam 602 is coupled to housing 400 at ends 604 and 606. End 604 includes hole 608, while end 606 includes hole 610. Pin 642 passes through hole 608, while pin 614 passes through hole 610 to couple flex beam 602 to housing 400. In this example, surface 614 is a surface of flex beam 602 that contacts the surface of an object. Flex beam 602 is flexible and capable of being contoured to the surface of an object in these examples. In other advantageous embodiments, a slot or a hole with a looser tolerance may be used on one or both ends of flex beam 602 to allow flex beam 602 to slide or move.

Housing 400 also includes channels 616 and 618. In these examples, channel 616 holds spring 620, while channel 618 holds spring 622. The shape of channel 616 and channel 618 may vary depending on the shape and dimensions of spring 620 and spring 622.

Spring 620 has end 624 connected to housing 400. End 626 of spring 622 is connected to housing 400. End 628 is connected to piston 630 while end 632 is connected to piston 634. These pistons serve as engagement members to engage surface 636 of flex beam 602. In these examples, channel 616, channel 618, spring 620, spring 622, piston 630, and piston 634 are part of a biasing unit to bias flex beam 602 towards the surface of an object. In some advantageous embodiments, flex beam 602 may have sufficient "spring back" properties that a biasing unit is unnecessary.

Figure 7:
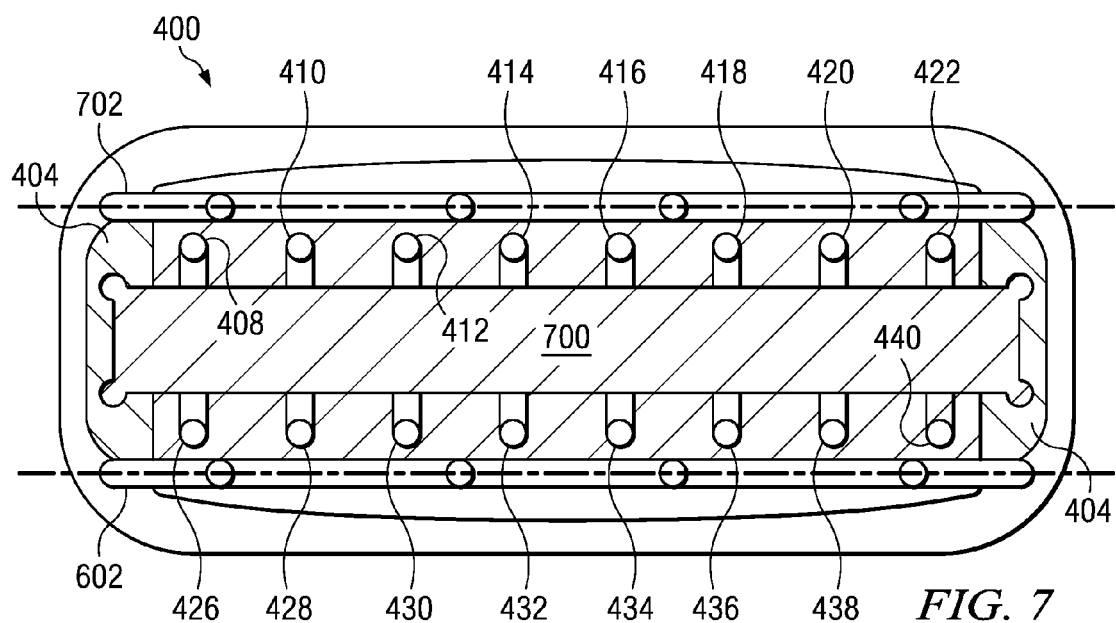
FIG. 7 is a bottom view of a housing in accordance with an advantageous embodiment.

Turning now to FIG. 7, a bottom view of housing 400 is depicted in accordance with an advantageous embodiment. In this example, a view of coupling region 700 can be seen. In this view, coupling region 700 is visible. Coupling region 700 is a region within housing 400 in which a coupling material may be present to couple transducers to the surface of the object. In these examples, engagement members, such as flex beam 602 and flex beams 702 are present to help create a seal within coupling region 700 to retain coupling material with coupling region 700. This seal may not be a watertight or liquid tight seal. This seal, however, is sufficient to retain the amount of coupling material needed by transducer to couple the transducer to the surface of the object being interrogated.

In this view, ports 408, 410, 412, 414, 416, 418, 420, 422, 424, 426, 428, 430, 432, 434, 436, 438, and 440 meet into coupling region 700 to provide a supply of coupling material for this region. As can be seen in this example, flex beam 602 and flex beam 702 help maintain the coupling material within coupling region 700. In fact, these flex beams and the two edges of the housing may define the coupling region and create a seal to maintain fluid within this region.

Figure 8:
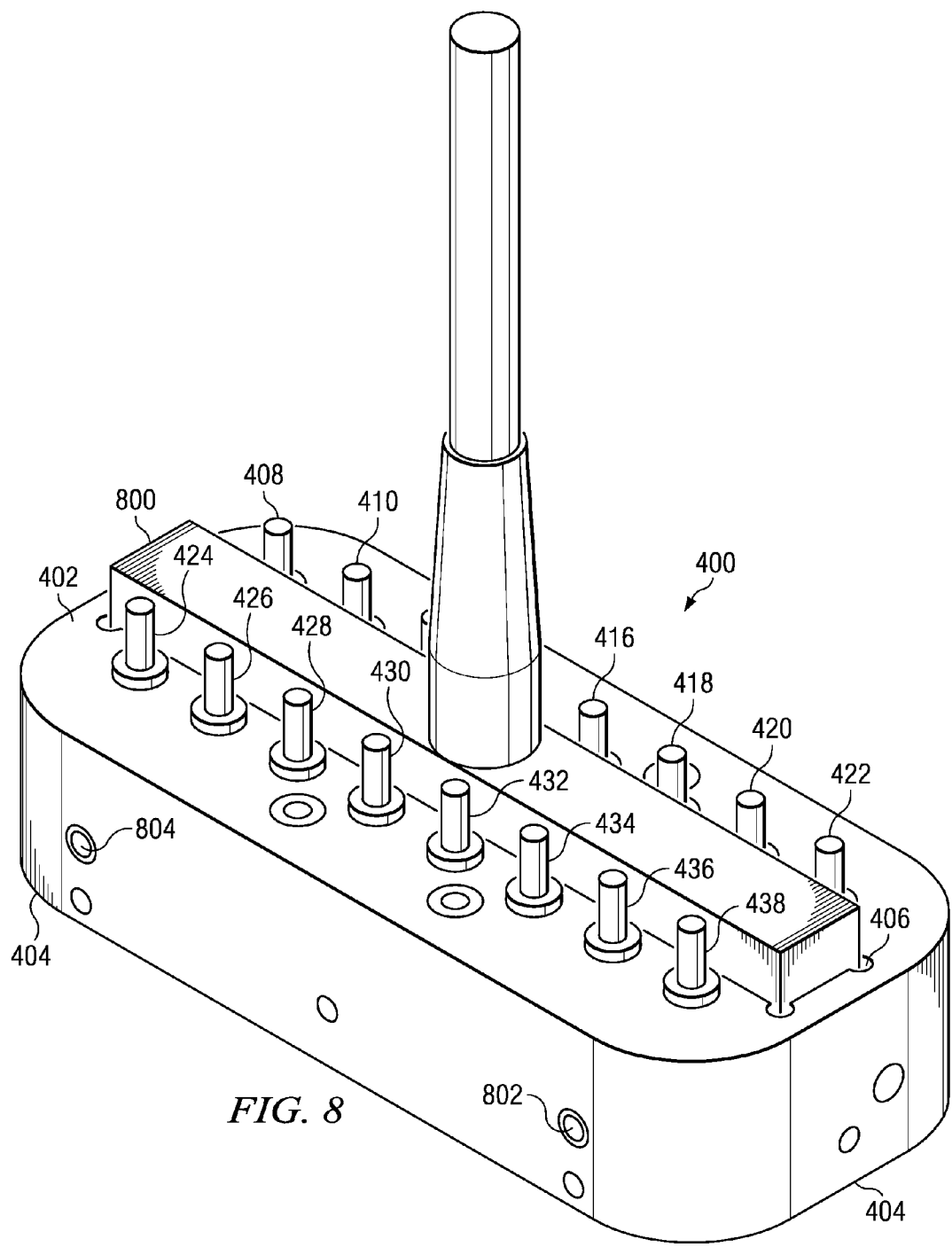
FIG. 8 is a diagram illustrating a perspective view of a housing with an ultrasonic unit in accordance with an advantageous embodiment.

With reference now to FIG. 8, a diagram illustrating a perspective view of a housing with an ultrasonic unit is depicted in accordance with an advantageous embodiment. In this example, ultrasonic unit 800 is placed into channel 406 in housing 400. Ultrasonic unit 800 is an array of transducers in these examples. Ultrasonic unit 800 also may be implemented using a single transducer depending on the particular implementation. Ultrasonic unit 800 may be held in place through some securing mechanism. In these examples, the securing mechanism takes the form of screws, such as screws 802 and 804. Additional screws may be located on side 806, which is not visible from this view of housing 400.

Figure 9:
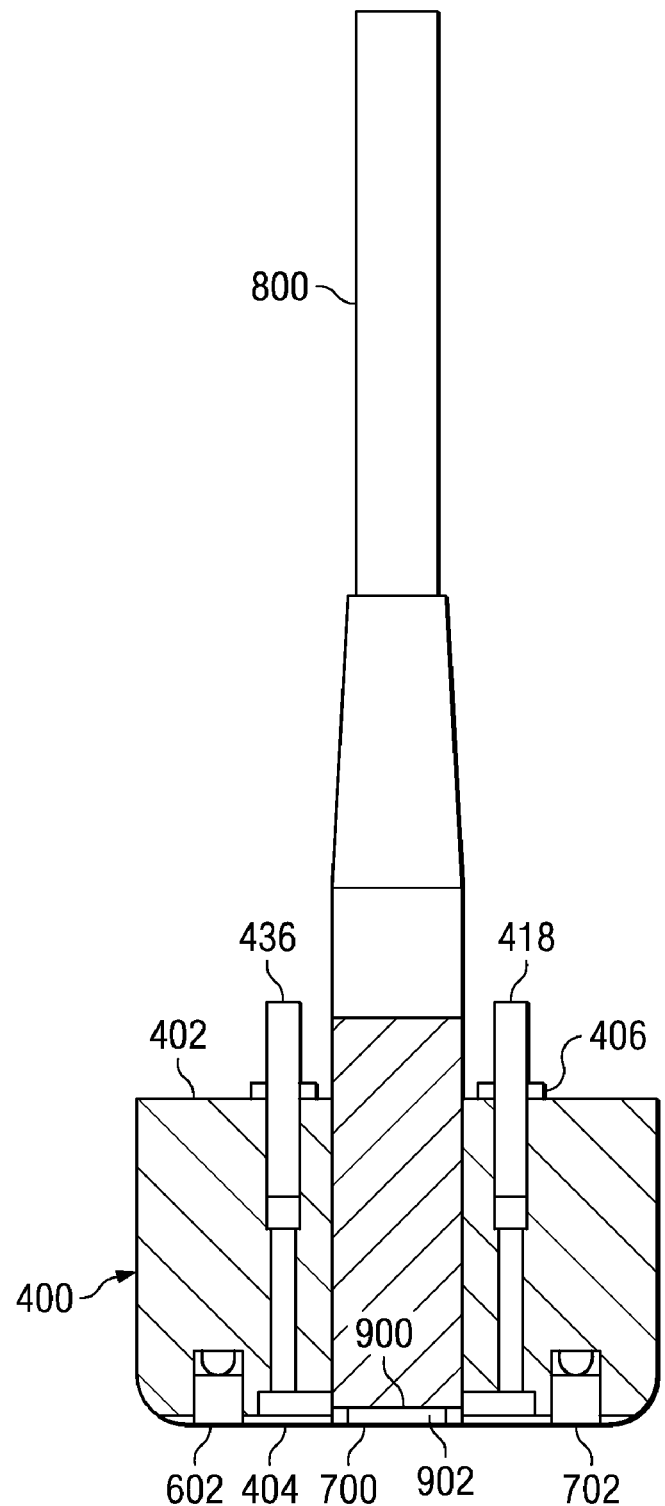
FIG. 9 is a cross-sectional view of a housing with a transducer unit in accordance with an advantageous embodiment.

Turning now to FIG. 9, a cross-sectional view of a housing with a transducer unit is depicted in accordance with an advantageous embodiment. In this example, transducer unit 800 is located in channel 406 between flex beams 602 and 702. As can be seen, side 900 of transducer unit 800 does not take up the entire portion of channel 406. Gap 902 is present between side 900 of transducer unit 800 and bottom 404. Gap 902 is located in part of coupling region 700.

As can be seen in this example, ports 434 and 418 may channel or supply coupling material into coupling region 700 between flex beams 602 and 702. In this manner, flex beams 602 and 702 are flexible and conformable to a surface on which housing 400 may be placed. With the seal, some coupling materials still may escape from coupling region 700. However, this seal formed with flex beam 602 and 702 retain some amount of a coupling material within coupling region 700 that is sufficient to couple transducer 800 to a surface of an object being interrogated.

Figure 10:
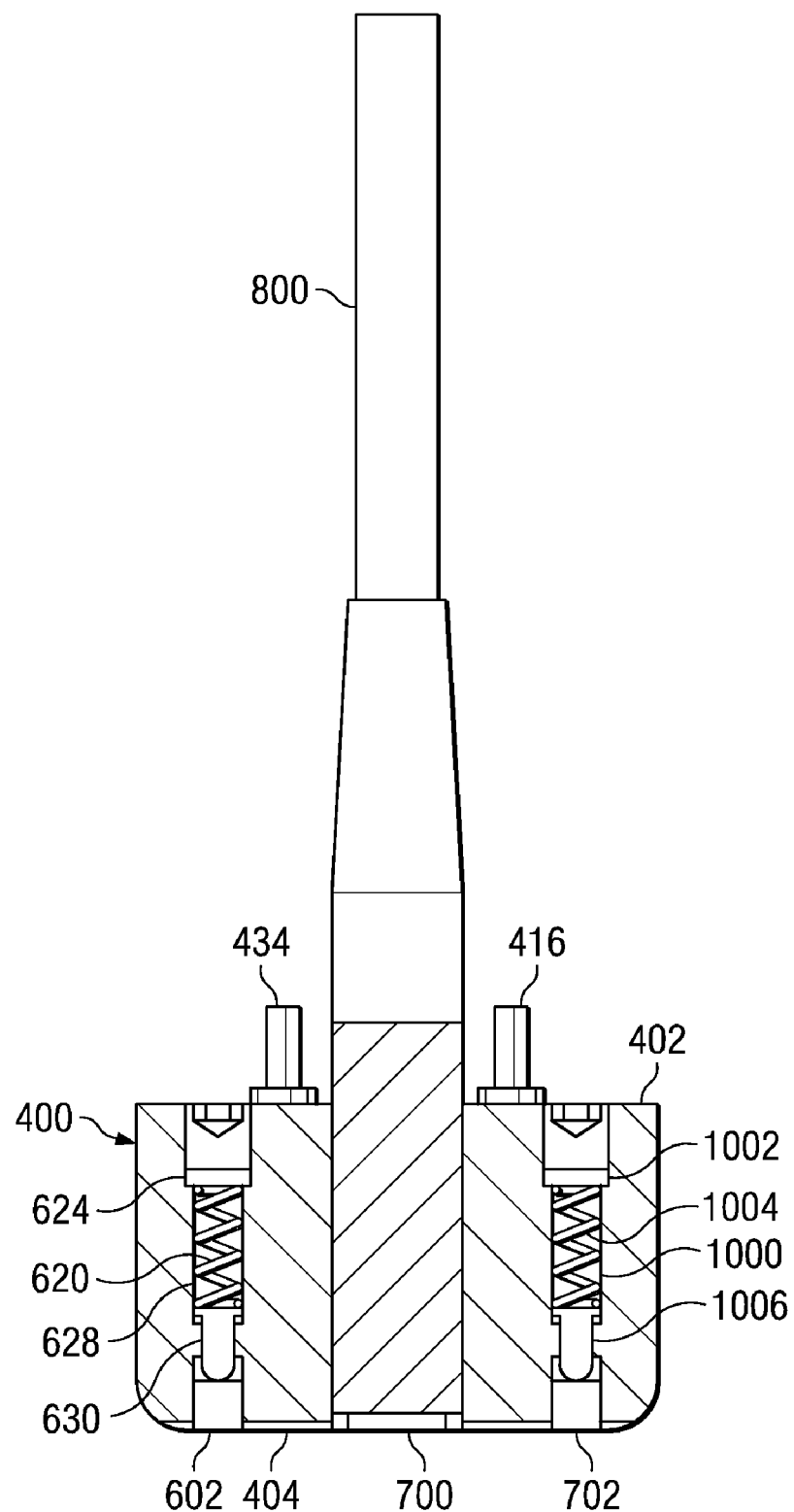
FIG. 10 is another cross-sectional view of a housing with a transducer unit in accordance with an advantageous embodiment.

With reference now to FIG. 10, another cross-sectional view of a housing with a transducer unit is depicted in accordance with an advantageous embodiment. In this example, another view of a biasing mechanism for flex beam 602 and 702 are illustrated. As can be seen in this particular view, spring 620 in channel 616 has one end connected to housing 400 and the second end connected to piston 630. In this example, another spring, spring 1000 is illustrated in which end 1002 is connected to housing 400 within channel 1003 and end 1004 connected to piston 1006. Pistons 630 and 1006 in turn are coupled to flex beams 602 and 702. In these examples, the coupling does not require one of these pistons to be secured or attached to flex beams. Instead, the coupling may occur from the contact of pistons 630 and 1002 to the surfaces of flex beams 602 and 702, respectively.

Figure 11:
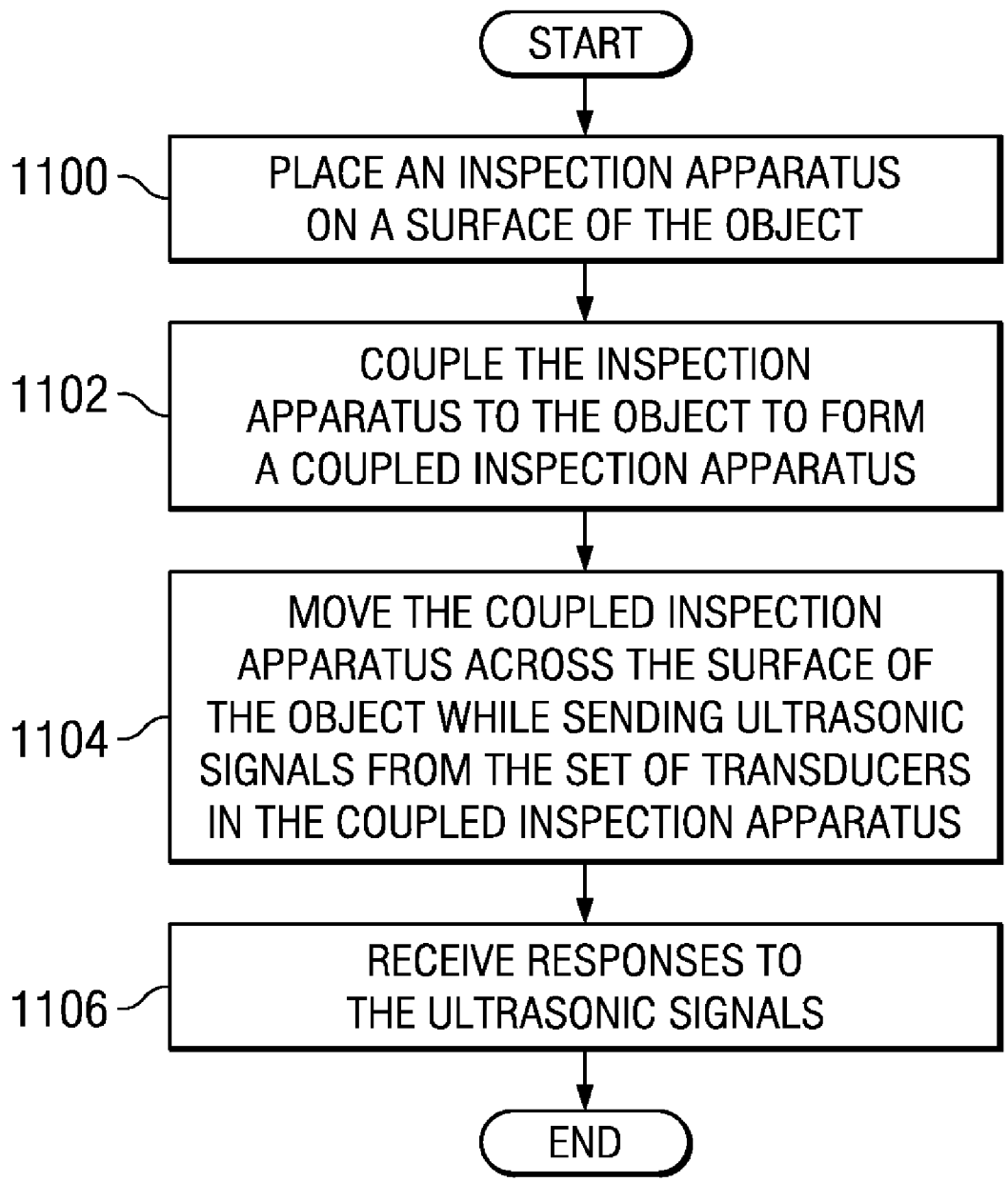
FIG. 11 is a flowchart of a process for inspecting an object in accordance with an advantageous embodiment.

With reference now to FIG. 11, a flowchart of a process for inspecting an object is depicted in accordance with an advantageous embodiment. The process illustrated in FIG. 11 may be implemented using an ultrasonic inspection apparatus, such as ultrasonic inspection apparatus 300 in FIG. 3.

The process begins by placing an inspection apparatus on the surface of the object (operation 1100). The object may be any object for which ultrasonic inspection is desired. The object may be, for example, without limitation, a composite aircraft fuselage, an aircraft wing panel, a control surface, an access panel, a sealed steel drum, a panel for an automobile, a concrete panel, or any other suitable object. In these examples, the inspection apparatus is ultrasonic inspection apparatus 300 in FIG. 3.

The process then couples the inspection apparatus to the object to form a coupled inspection apparatus (operation 1102). In operation 1102, a coupling material may be introduced into a coupling region within the inspection apparatus to couple an ultrasound unit in the inspection apparatus to the object. The process then moves the coupled inspection apparatus across the surface of the object while sending ultrasonic signals from the set of transducers in the coupled inspection apparatus (operation 1104). The process receives responses to the ultrasonic signals (operation 1106) with the process terminating thereafter. Of course different operations may be performed at the same time or in different orders. For example, the coupling and moving operations may be performed at the same time. Further, the sending of ultrasonic signals and receipt of responses to those signals in operations 1104 and 1106 may occur at the same time.

Thus, the different advantageous embodiments provide a method and apparatus for placing a set of ultrasonic transducers in a position generally adjacent to a surface of an object. The use of the term "set" refers to a set of one or more items.

For example, a set of ultrasonic transducers is one or more transducers. In these examples, the ultrasonic inspection apparatus has a body, a set of engagement members, and a set of ports. The body has a contact surface capable of contacting the surface of the object in which the body is capable of holding the set of ultrasonic transducers.

The set of engagement members are connected to the body for engagement with the surface of the object and the set of engagement members is flexibly bendable and is capable of conforming to contours across the surface of the object to form a coupling region within the body. The set of ports are capable of delivering a coupling material to a coupling region. The set of engagement members when in contact with the surface of the object causes a seal to attain an amount of the coupling material within the coupling region sufficient to couple a set of ultrasonic transducers to the surface of the object.

Through the use of engagement members that are flexible and capable of conforming to the surface of an object, some of the different advantageous embodiments are able to maintain a coupling material in an amount sufficient to couple a transducer to the surface of an object. In the different advantageous embodiments, these flexible engagement members may be flex beams in a housing that attains coupling material by bending to conform to various cylindrical and radius surfaces then straighten out when the surfaces become flat. This conformability may occur through the flexibility of the flex beams. Additionally, the use of a biasing mechanism also may aid to maintain this conformability.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An ultrasonic inspection apparatus for placing a set of ultrasonic transducers at a position generally adjacent to a surface of an object, the ultrasonic inspection apparatus comprising:
   a body having a contact surface capable of contacting the surface of the object, wherein the body is capable of holding the set of ultrasonic transducers;
   a set of engagement members connected to the body for engagement with the surface of the object, wherein the set of engagement members is flexibly bendable and is capable of conforming to contours across the surface of the object to form a coupling region within the body;
   wherein the set of engagement members comprises: a first beam; and a second beam, wherein the first beam and the second beam are connected to the body parallel to each other and wherein the coupling region is located between the first beam and the second beam; and
   a set of ports capable of delivering a coupling material to the coupling region and wherein the set of engagement members, when in contact with the surface of the object, causes a seal to retain an amount of the coupling material within coupling region sufficient to couple the set of ultrasonic transducers to the surface of the object.

2. The ultrasonic inspection apparatus of claim 1, wherein the set of engagement members is selected from one of a set of plastic engagement members and a set of metal engagement members.

3. The ultrasonic inspection apparatus of claim 1 further comprising:
   a set of springs, wherein the set of springs has a first end connected to the body and a second end coupled to the set of engagement members and wherein the set of springs biases the set of engagement members towards the surface of the object.

4. The ultrasonic inspection apparatus of claim 3, wherein the set of spring are located in a set of channels in the body and wherein the second end of the set of springs is connected to the set of engagement members by a set of plungers through contact between the set of engagement members and the set of plungers such that the set of springs remain within the set of channels.

5. The ultrasonic inspection apparatus of claim 1 further comprising;
   the set of ultrasonic transducers connected to the body.

6. The ultrasonic inspection apparatus of claim 1, wherein the first beam has a first hole at a first end of the first beam connected to the body with a first pin and a second hole at a second end of the first beam connected to the body with a second pin and wherein the second beam has a third hole at a first end of the second beam connected to the body with a third pin and a fourth hole at a second end of the second beam connected to the body with a fourth pin.

7. The ultrasonic inspection apparatus of claim 1, wherein the object is selected from one of a composite aircraft fuselage, an aircraft wing panel, and a sealed drum.

8. An apparatus comprising:
   a housing having a contact surface capable of contacting a surface of an object, wherein the housing is capable of holding a set of ultrasonic transducers; and
   a set of engagement members coupled to the housing, wherein the set of engagement members is capable of engaging the surface of the object, wherein the set of engagement members is flexibly bendable and is capable of conforming to contours across the surface of the object to form a coupling region in which a coupling material can be retained when the contact surface of the housing is in contact with the surface of the object; and
   wherein the set of engagement members comprises: a first beam; and a second beam, wherein the first beam and the second beam are connected to the body parallel to each other and wherein the coupling region is located between the first beam and the second beam.

9. The apparatus of claim 8 further comprising:
   a set of ports capable of delivering a coupling material to the coupling region and wherein the set of engagement members, when the set of engagement members causes the body to retain a sufficient amount of the coupling material within coupling region to couple the set of ultrasonic transducers to the surface of the an object to send signals into object and receive ultrasonic signals from an object.

10. The apparatus of claim 8, wherein the first beam has a first hole at a first end of the first beam connected to the body with a first pin and a second hole at a second end of the first beam connected to the body with a second pin and wherein the second beam has a third hole at a first end of the second beam connected to the body with a third pin and a fourth hole at a second end of the second beam connected to the body with a fourth pin.

11. The apparatus of claim 8 further comprising:
a biasing unit coupled to the housing and to the set of engagement members, wherein the biasing unit biases the set of engagement members to conform to contours across the surface of the object to form the coupling region.

12. The apparatus of claim 11, wherein the apparatus comprises:
wherein a set of springs are located in a set of channels in the housing and wherein a second end of the set of springs is connected to the set of engagement members by a set of plungers through contact between the set of engagement members and the set of plungers such that the set of springs remain within the set of channels.

13. The apparatus of claim 8, wherein the object is selected from one of a composite aircraft fuselage, an aircraft wing panel, and a sealed drum.

14. The apparatus of claim 8, wherein the set of transducers is a plurality of transducers arranged in an array.

15. A method for inspecting an object comprising:
placing an inspection apparatus on a surface of the object, wherein the inspection apparatus comprises a set of transducers; a body having a contact surface capable of contacting the surface of the object, wherein the body is capable of holding the set of ultrasonic transducers; and a set of engagement members coupled to the body for engagement with the surface of the object, wherein the set of engagement members is flexibly bendable and is capable of conforming to contours across the surface of the object to form a coupling region within the body; and a set of ports capable of delivering a coupling material to the coupling region and wherein the set of engagement members, when the set of engagement members when in contact with the surface of the object causes a seal to retain an amount of the coupling material within the coupling region sufficient to couple the set of ultrasonic transducers to the surface of the object to send signals into the object and receive ultrasonic signals from the object; and wherein the set of engagement members comprises: a first beam; and a second beam, wherein the first beam and the second beam are connected to the body parallel to each other and wherein the coupling region is located between the first beam and the second beam;
coupling the inspection apparatus to the object to form a coupled inspection apparatus;
sending ultrasonic signals from the set of transducers in the coupled inspection apparatus; and
receiving responses to the ultrasonic signals.

16. The method of claim 15 further comprising:
moving the coupled inspection apparatus across the surface of the object while sending ultrasonic signals from the set of transducers in the coupled inspection apparatus and receiving responses to the ultrasonic signals.

17. The method of claim 15, wherein the coupling step comprises:
sending the coupling material into the ports to enter the coupling region, wherein the set of transducers are coupled to the surface of the object.

18. The method of claim 15, wherein the object is selected from one of a composite aircraft fuselage, an aircraft wing panel, and a sealed drum.

* * * * *